United States Patent [19]

Richmond et al.

[11] Patent Number: 5,022,538

[45] Date of Patent: Jun. 11, 1991

[54] I.V. BAG ORGANIZER

[75] Inventors: Frank M. Richmond, Harvard, Ill.; Timothy Vanderveen, Poway, Calif.

[73] Assignee: Fisher Scientific Company, Pittsburgh, Pa.

[21] Appl. No.: 441,960

[22] Filed: Nov. 28, 1989

[51] Int. Cl.$^5$ .............................................. A47F 7/00
[52] U.S. Cl. .................................... 211/113; 211/13
[58] Field of Search ................... 211/113, 123, 13, 71, 211/59.1, 12, 88; 24/601.7; 248/317; 281/21.1, 15.1; 402/80 P; 604/322, 403

[56] References Cited

U.S. PATENT DOCUMENTS

| | | | |
|---|---|---|---|
| 917,949 | 4/1909 | Jacky et al. | 24/601.7 |
| 3,460,789 | 8/1969 | McKirdy et al. | 211/113 X |
| 4,374,627 | 2/1983 | Friedman | 402/80 P |
| 4,500,223 | 2/1985 | Downing et al. | 402/80 P |
| 4,856,744 | 8/1989 | Frankel | 211/113 X |

Primary Examiner—Alvin C. Chin-Shue
Assistant Examiner—Sarah A. Lechok
Attorney, Agent, or Firm—Nydegger & Associates

[57] ABSTRACT

An apparatus and method for organizing and hanging a plurality of I.V. bags on an I.V. pole includes a solid back and a plurality of spaced apart resilient loops, which apparatus fits over a horizontal support bar on the I.V. pole. The resilient loops are movable between an open position and a closed position. The loops are biased to be in the closed position normally, with a free end of the loop overlapping the top edge of the back. The loop is moved to the open position to place I.V. bags onto the loops, and suspend the I.V. bags at spaced apart intervals in organized fashion. The apparatus includes an unobstructed span having a restraining member to secure the apparatus to the I.V. pole. Some or all loops may include locking members to lock the loops in the closed position.

20 Claims, 2 Drawing Sheets

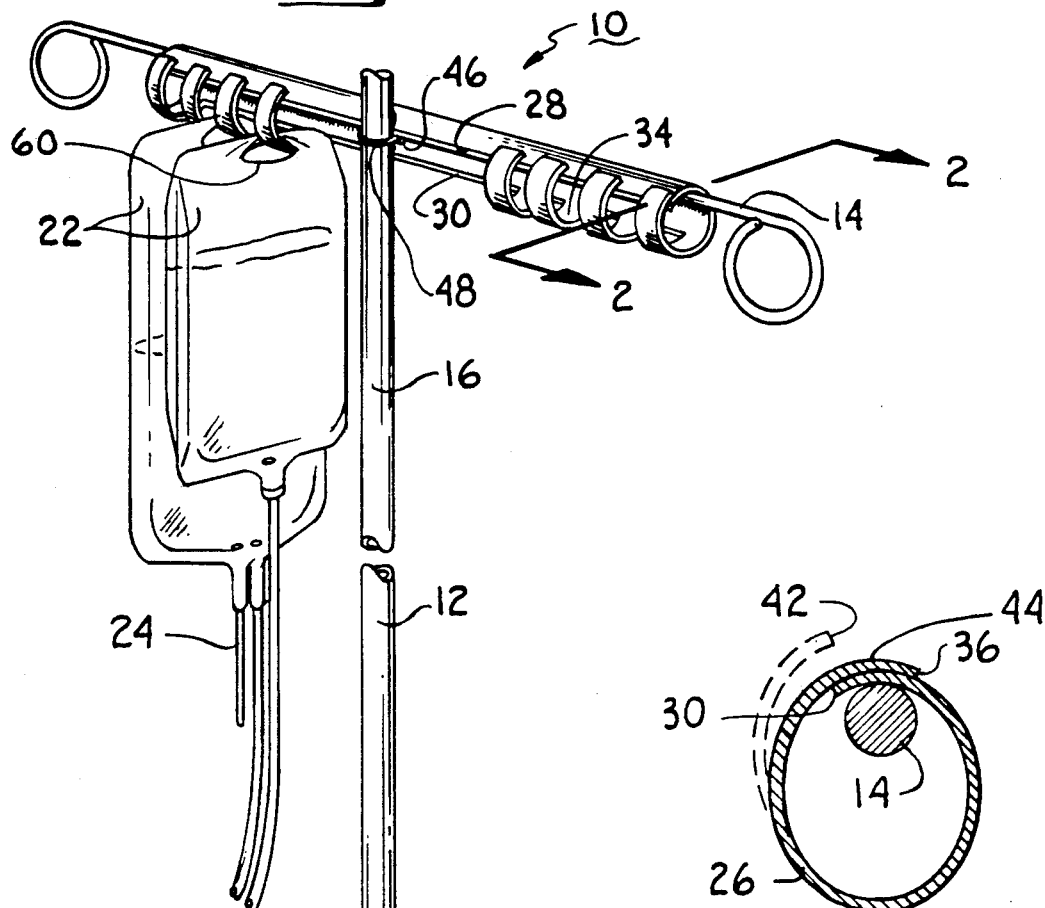
Fig. 1
Fig. 2
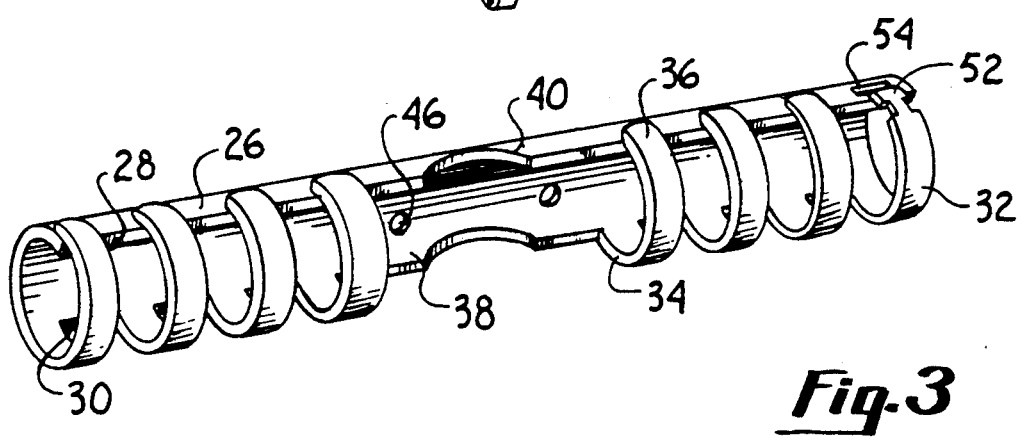
Fig. 3

I.V. BAG ORGANIZER

FIELD OF THE INVENTION

This invention relates generally to apparatus for intravenous (I.V.) infusion of fluidized medicaments to a patient. More specifically, the invention relates to an apparatus for organizing and hanging I.V. fluid sources which are connected to infusion devices. The present invention is particularly, though not exclusively, useful for organizing and hanging a plurality of I.V. bags on an I.V. pole in a hospital or home care environment.

BACKGROUND OF THE INVENTION

Intravenous infusion of fluidized medicaments to a patient typically involves connecting a fluid source to an I.V. fluid infusion device, such as an I.V. pump, which is in turn connected in fluid communication with the patient. The I.V. fluid source is generally an I.V. bag or container which holds the fluidized medicament that is fed through a tube to the infusion device. The I.V. bag is typically suspended above the patient on a support member, such as an I.V. pole. A conventional I.V. pole is typically an X-shaped or T-shaped apparatus having a horizontal support bar connected to a vertical support member. The I.V. pole is typically made of stainless steel, and may have a base with wheels so it may be moved about the hospital environment as needed to accommodate movement of the patient. Further, the conventional I.V. pole normally has a spiral hook formed on each end of the horizontal support bar. Typically, I.V. bags have a premeasured amount of fluid sealed in the I.V. bag. An opening is formed in the top of the sealed I.V. bag, so the opening may be placed over the spiral hook to suspend the bag on the I.V. pole. The suspended bag may then be connected to an infusion device which device is typically mounted below the I.V. bag, either on a lower portion of the vertical support member of the same I.V. pole, or on a separate infusion device support stand. In any event, such conventional I.V. poles typically have only two hooks for suspending I.V. bags, one at each end of the horizontal bar.

In certain instances in the treatment of patients, it becomes necessary to connect a plurality of I.V. bags in fluid communication to the same infusion device. This requires suspending a plurality of such bags above the device. Unfortunately, such conventional I.V. poles having only two hooks can conveniently accommodate only two I.V. bags at a time. It is possible to hang more than one bag on each hook to suspend more than two bags, but this arrangement has several disadvantages. One disadvantage is that when multiple I.V. bags are suspended from one hook, the bags hang against one another and the tubes leading from the bottom of the bags to the infusion device can become entangled with each other. Aside from causing inconvenience and inefficiencies in the handling of the I.V. bags by hospital staff, the tubes can get intertwined and become obstructed. In addition, the tangled plurality of tubes can make it difficult to properly identify which tube is connected to which I.V. bag. This may result in incorrect connection to the infusion device, having potentially catastrophic effects on the patient. The potential for entanglement of tubes from multiple I.V. bags hanging on the same hook also reduces the speed with which various bags can be changed by hospital staff. This also translates into additional time and costs, and can, in some instances, be life threatening.

A further disadvantage of suspending multiple I.V. bags on one hook with conventional I.V. poles is the potential for uneven weight distribution on the horizontal bar. Having a requirement for an odd number of bags, or of multiple bags of different sizes containing differing amounts of fluid, can result in different amounts of weight on the spiral hook at each end of the horizontal bar. The effect of the difference in weight at each end is magnified by the length of the horizontal bar which creates an unwanted moment arm. This in conjunction with the height at which the bags are suspended on the I.V. pole contributes to an unstable condition in which the I.V. pole could be more inclined to topple over, especially during transport.

The present invention thus recognizes the need for an apparatus for organizing and hanging a plurality of I.V. bags. The present invention further recognizes that there currently exist many conventional I.V. poles, and that there is a need to supply a bag organizer apparatus which can readily be adapted to such conventional I.V. poles.

Accordingly, it is an object of the present invention to provide an apparatus for organizing and hanging a plurality of fluid source bags on a conventional I.V. pole. It is yet another object of the present invention to provide a fluid bag organizer apparatus which is relatively inexpensive to manufacture, and simple and convenient to use in a hospital environment. It is another object of the present invention to provide a fluid bag organizer apparatus which permits a plurality of I.V. bags to be suspended at spaced apart intervals.

SUMMARY OF THE INVENTION

A preferred embodiment of the I.V. bag organizer includes a long, slender hollow tubular member having a solid back portion. The solid back portion has a top edge and a bottom edge. A plurality of semi-rigid resilient loops are connected to the bottom edge of the solid back at spaced apart intervals and each resilient loop has a free end which is movable between an open position and a closed position. The loop is resiliently biased toward the closed position. The back and loops may be formed integrally. In the closed position, the free end of the loop engages the top edge of the solid back so that the free end of the loop overlaps the solid back to form a closed loop. In the open position, the free end of the loop is pulled away so the free end is disengaged from the back. The solid back also has an unobstructed span portion across which no loops are attached.

The tubular member is placed on an I.V. pole of the type having a horizontal support bar connected to a vertical support member. The hollow tubular member is oriented so the top edge of the back portion is supported by the horizontal bar. The free ends of the loops overlap the top edge of the back portion, and the unobstructed span portion is positioned against the vertical support member. The span portion has a strap attached which may be fastened about the vertical member of the I.V. pole to secure the tubular member to the I.V. pole. In one embodiment, the span is located in the center of the tubular member, with loops spaced apart on either side of the span to support I.V. bags along the entire length of the horizontal bar. In another embodiment, the span is at one end of the tubular member, with loops spaced apart on one side of the span to support I.V. bags along one-half of the horizontal bar. The loops may include a locking element for locking the free end of the loop to the top edge of the back in the closed position. I.V. bags can be conveniently organized and suspended on the loops by grasping and moving the desired loop to the open position, sliding the opening at the top of the I.V. bag onto the loop, and allowing the loop to spring back to its closed position.

The novel features of this invention, as well as the invention itself, both as to its structure and its operation, will be best understood from the accompanying drawings, taken in conjunction with the accompanying description, in which similar reference characters refer to similar parts, and in which:

BRIEF DESCRIPTION OF THE DRAWINGS

FIG. 1 is a front perspective view of an apparatus for organizing and hanging I.V. bags shown on an I.V. pole in its intended environment;

FIG. 2 is an end cross-sectional view taken along the line 2—2 of the apparatus shown in FIG. 1;

FIG. 3 is another perspective view of the apparatus shown in FIG. 1;

DETAILED DESCRIPTION OF THE PREFERRED EMBODIMENT

Figure 6:
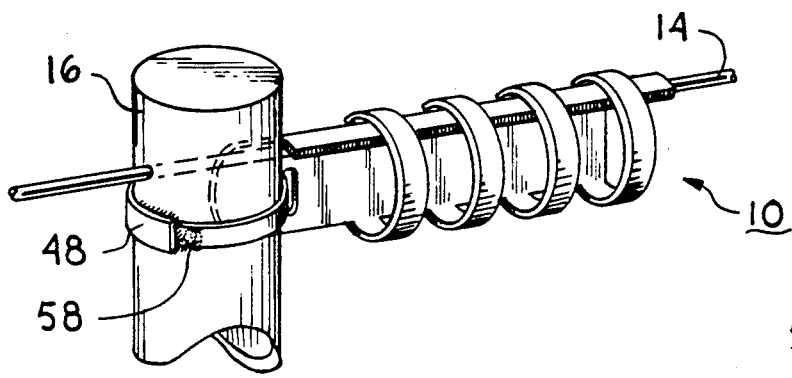
FIG. 6 is a perspective view of yet another embodiment of the apparatus of the present invention.

Referring now to FIG. 1, there is shown an apparatus, generally designated 10, for organizing and hanging a plurality of I.V. bags, being shown in its intended environment. Apparatus 10 has a hollow, slender tubular shape, and is shown mounted on an I.V. pole 12. I.V. pole 12, in the embodiment shown, has a horizontal support bar 14 rigidly connected to a vertical support member 16. I.V. pole 12 also includes legs 18 having wheels 20 for moving the I.V. pole about. Bag organizer apparatus 10 supports I.V. fluid sources or bags 22, each of which has a fluid tube 24 for use in the medical infusion process.

Referring further to FIGS. 2 and 3 there is shown bag organizer apparatus 10 comprising a solid base or back portion 26, with a top edge 28 and a bottom edge 30. Bag organizer apparatus 10 may advantageously be made of a semi-rigid resilient material, such as plastic, which is sturdy, yet light-weight. Such material may also advantageously be made of a material which can withstand the sterilization process if needed. As shown in FIG. 2, an end cross section shows the apparatus 10 has an oval shape. Various other configurations could be used if the other configurations have an inside shape sufficient to permit placing the apparatus over horizontal bar 14 of I.V. pole 12.

Connected to bottom edge 30 of solid back 26 are a plurality of semi-rigid resilient hooks or loops 32. Each loop 32 has a fixed end 34 which is rigidly attached to back 26, and a free end 36. Loops 32 are attached at spaced apart intervals to accommodate the particular size of the I.V. pole 12, as well as the sizes and desired separation of bags 22 to be used in the infusion process. In the embodiment shown in FIGS. 1, 2 and 3, there are six loops 32, with two groups of three spaced evenly apart symmetrically about vertical member 16 bag organizer apparatus 10. A portion of back 26 includes an unobstructed span portion 38 where no loops 32 are attached. Span 38 is of sufficient width to permit vertical member 16 of I.V. pole 12 to be positioned against span 38 so apparatus 10 fits properly onto I.V. pole 12. Along span 38 there is an indented portion 40, which is formed in top edge 28 of base 26 to further minimize interference with vertical support member 16.

Loops 32 are made of strong resilient material, capable of supporting the weight of fluid filled I.V. bags 22, yet are flexible. In particular, each loop 32 has a free end 36 which, as illustrated in FIG. 2, is movable between an open position 42 to allow I.V. bags 22 to be added or removed from the apparatus 10, and a closed position 44 for securely retaining the bags 22 in a suspended position in organized fashion. The loops 32 of apparatus 10 are normally in the closed position 44, since loops 32 are resiliently based to cause free end 36 to engage and overlap top edge 28 of back 26. The amount of overlap preferably is sufficient to allow a free end 36 of loop 32 to lap over horizontal bar 14 and top edge 28 of back 26, to bear the weight of bags 22 beneath horizontal bar 14. To further increase the weight bearing capacity of loops 32, back 26 may be formed with a plurality of slots (not shown) into which free ends 36 of loops 32 may be inserted when the loops are in their closed positions 44.

As further shown in FIGS. 1 and 3, at span 38 there are holes 46. A restraining member 48, such as a tie strap as shown in the preferred embodiment, can be placed through holes 46 and wrapped around vertical support member 16 to stabilize bag organizer apparatus 10 on I.V. pole 12. The strap may be held in place by conventional tie straps, hook and pile fasteners, or pop rivets. Further shown in FIG. 3 are certain loops 32 having a locking member 50. Locking member 50 includes a detent or catch 52 which fits into a notched hole 54 to lock loop 32 securely in place.

Figure 4:
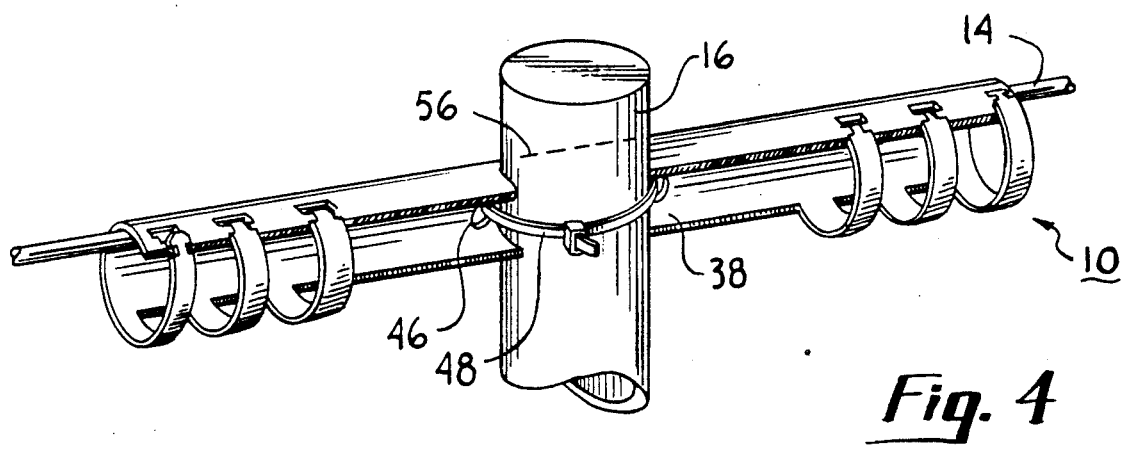
FIG. 4 is a perspective view of one embodiment of the apparatus according to the present invention.
Figure 5:
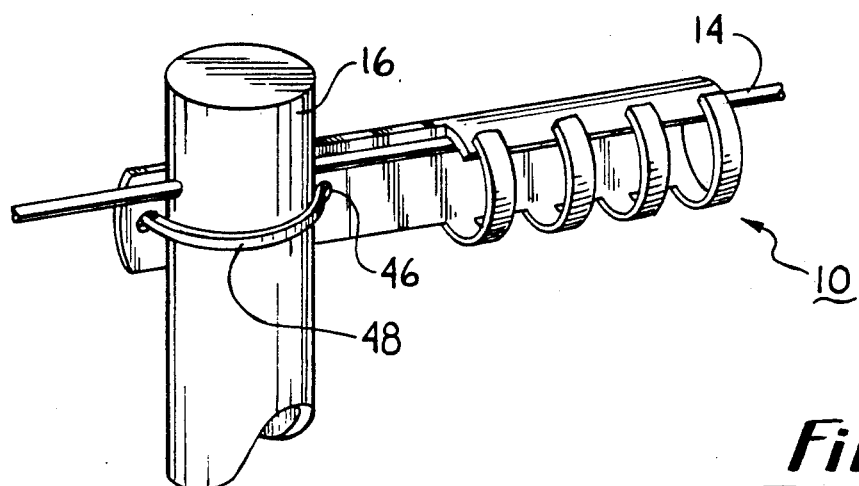
FIG. 5 is a perspective view of another embodiment of the apparatus of the present invention.

FIGS. 4, 5 and 6 show alternative embodiments of the present invention. FIG. 4 shows a bag organizing apparatus 10 having an unobstructed span 38 in central portion 56, with an equal number of loops 32 spaced equally apart on either side of central portion 56. This embodiment includes two holes 46 for strap 48. FIG. 5 illustrates an alternative embodiment in which there is sufficient length of back 26 to cover all or a portion of one side of horizontal bar 16. Span 38 still has two holes 46 for strap 48 to secure bag organizer 10 to vertical support member 16. FIG. 6 is yet another embodiment in which one side of horizontal bar 16 is covered, and there is one hole 46 for attaching strap 48 about vertical support member 16. Also in the embodiment of FIG. 6, there is shown a releasable hook and pile (e.g. Velcro) fastener 58.

In operation according to the present invention, the user places the bag organizer apparatus, which may have been previously sterilized, over horizontal bar 14. This is accomplished by moving each of loops 32 to the open position 42, placing back 26 into bar 14, and allowing loops 32 to close. Locking members 50 may be locked in position appropriately. Once the user has determined where each bag 22 is to be suspended, the user opens the free end 36 of each of desired loops 32. The user then places bag opening 60 at top of bag 22 over free end 36, to suspend bag 22 from fixed end 34 of loop 32. Upon release of free end 36, loop 32 moves to the closed position 44 to suspend bags 22 in spaced apart intervals in organized fashion on I.V. pole 12.

While the particular I.V. bag organizer as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

What is claimed is:

1. An apparatus for organizing and hanging a plurality of I.V. bags at spaced apart locations on an I.V. pole, of the type having a horizontal support bar connected to a vertical support member, comprising:
   a back having a top edge and a bottom edge;
   a plurality of resilient loops integrally attached to said bottom edge, said loops being biased to extend from said bottom edge and overlap said top edge to create a substantially hollow tubular-shaped member positionable about said support bar;
   a span extending along said back; and
   means for securing said span to said vertical support member.

2. An apparatus for organizing and hanging a plurality of I.V. bags as recited in claim 1, wherein at least one of said loops has a free end distanced from said bottom edge, and said apparatus further comprises means for locking said free end to said top edge.

3. An apparatus for organizing and hanging a plurality of I.V. bags as recited in claim 1, wherein said means for securing comprises said span having holes, and a tie strap positioned through said holes.

4. An apparatus for organizing and hanging a plurality of I.V. bags as recited in claim 3, wherein said tie strap is secured to said vertical support member by a releasable fastener attached to said vertical support member.

5. An apparatus for organizing and hanging a plurality of I.V. bags as recited in claim 1, wherein said back and loops are made of plastic material.

6. An apparatus for organizing and hanging a plurality of I.V. bags as recited in claim 1, wherein said span is located substantially in the middle of said back.

7. An apparatus for organizing and hanging a plurality of I.V. bags as recited in claim 1, wherein said span is located substantially at one end of said back.

8. An apparatus for organizing and hanging a plurality of I.V. bags on an I.V. pole of the type having a horizontal support bar connected to a vertical support member, comprising:
   a base having a bottom edge and a top edge;
   a plurality of semi-rigid resilient loop members each having one end integrally connected to said bottom edge and having a free end engageable with said top edge, each said loop being biased to overlap said top edge, said plurality of loops further being connected along said bottom edge of said base portion at spaced apart intervals; and
   an unobstructed span extending along said base to permit placing said tubular member over said horizontal support bar with said vertical support bar positioned in said span.

9. An apparatus for organizing and hanging a plurality of I.V. bags as recited in claim 8, further comprising stabilizing means associated with said span for securing said span to said vertical support member.

10. An apparatus for organizing and hanging a plurality of I.V. bags as recited in claim 9, wherein said stabilizing means comprises holes in said span for attaching a strap.

11. An apparatus for organizing and hanging a plurality of I.,V. bags as recited in claim 9, wherein said stabilizing means comprises a strap releasably attached to said vertical support member.

12. An apparatus for organizing and hanging a plurality of I.V. bags as recited in claim 8, further comprising means for locking said free end to said top edge.

13. An apparatus for organizing and hanging a plurality of I.V. bags as recited in claim 8, wherein said span is located substantially in the middle of said base.

14. An apparatus for organizing and hanging a plurality of I.V. bags as recited in claim 8, wherein said span is located substantially at one end of said base.

15. A method of organizing and hanging a plurality of I.V. bags at spaced apart locations on a horizontal bar of an I.V. pole, comprising the steps of:
   providing a solid back, having a top edge and a bottom edge, and further having a plurality of spaced apart resilient loops, said loops each having a fixed end integrally connected to said bottom edge and a free end, said free end being movable between a closed position wherein said free end is biased to overlap said top edge; and an open position wherein said free end is pulled away from said top edge; and
   placing said back onto said horizontal bar so that said loops are oriented with said fixed ends being positioned below said free ends.

16. A method of organizing and hanging a plurality of I.V. bags as recited in claim 15, further comprising the step of fastening said back to said I.V. pole.

17. A method of organizing and hanging a plurality of I.V. bags as recited in claim 16, further comprising the step of locking said free end in said closed position.

18. A method of organizing and hanging a plurality of I.V. bags as recited in claim 15, further the steps of:
   moving said free end of one of said loops to said open position;
   placing one of the I.V. bags on said free end of said one loop; and
   moving said free end of said one loop to said closed position.

19. A method of organizing and hanging a plurality of I.V. bags as recited in claim 18, wherein a plurality of I.V. bags are placed on said loops at sufficient distances apart to prevent the I.V. bags from touching one another.

20. A method of organizing and hanging a plurality of I.V. bags as recited in claim 15, further comprising the step of sterilizing said back prior to placing said back over said horizontal bar.

* * * * *